(12) United States Patent
Jo et al.

(10) Patent No.: US 6,523,546 B2
(45) Date of Patent: Feb. 25, 2003

(54) PEDICURE SANDER HAVING SHOCK-ABSORBING UNIT

(76) Inventors: Jeom-Sup Jo, 92-11 35th Ave., #5C, Jackson Heights, NY (US) 11372; Ik-Joon Jo, Sam-ik Beach 202-205 148 Namcheon2-dong, Nam-koo, Pusan (KR)

( * ) Notice: Subject to any disclaimer, the term of this patent is extended or adjusted under 35 U.S.C. 154(b) by 126 days.

(21) Appl. No.: 09/758,278

(22) Filed: Jan. 12, 2001

(65) Prior Publication Data
US 2002/0050278 A1 May 2, 2002

(30) Foreign Application Priority Data
Oct. 31, 2000 (KR) .................................... 2000-0030364

(51) Int. Cl.⁷ ............................................. A45D 29/05
(52) U.S. Cl. ........................ 132/75.8; 132/76.4; 132/75; 606/131
(58) Field of Search ............................. 132/75.8, 73.6, 132/75.6, 76.4, 75; 451/358, 444, 496, 497, 454, 519; 433/125, 142, 166; 15/256.51; 606/131, 133

(56) References Cited
U.S. PATENT DOCUMENTS 1,011,573 A * 12/1911 Butler ........................ 451/456
2,056,379 A * 10/1936 Acocella .................... 132/73.6
4,536,994 A * 8/1985 Krebs .......................... 51/328

* cited by examiner

Primary Examiner—Todd E. Manahan
Assistant Examiner—David Comstock
(74) Attorney, Agent, or Firm—Harrison & Egbert

(57) ABSTRACT

A pedicure sander, used for a removal of calluses or corns from the hands or the feet, includes a cylindrical rotary body encased in a safety housing, and two abrasive sheets closely covering the external surface of the rotary body while being individually fixed to two fixing grooves of the body. The rotary body is rotatable by a drive motor seated within a handle of the sander. A support bracket rotatably holds the opposite ends of the drive shaft of the rotary body and has two different-sized openings on its bottom surface. A flake brush is hinged to the bracket at the bristle part to remove deposited flakes of epidermis from the filing surface of the abrasive sheet. A torsion spring is held against both the flake brush and the support bracket at its opposite arms. A shock absorbing unit is provided at each end of the drive shaft. This shock absorbing unit includes a support bushing and a support spring.

1 Claim, 5 Drawing Sheets

US 6,523,546 B2

PEDICURE SANDER HAVING SHOCK-ABSORBING UNIT

BACKGROUND OF THE INVENTION

1. Field of the Invention

The present invention relates to a pedicure sander used for care and treatment of the hands or the feet, for removal of calluses or corns from the hands or feet, and, more particularly, to a pedicure sander, with a motorized rotary body fixedly covered with abrasive sheets and protected by a safety housing, having a plurality of different-sized openings formed on its bottom surface, thus allowing a user to effectively remove a callus or a corn from the hands or the feet using an abrasive sheet partially exposed through a proper one of a large or small opening in accordance with a size of an area around the callus or the corn.

2. Description of the Related Art

As well known to those skilled in the art, thick calluses or corns are typically formed on the palms of the hands or the soles of the feet when the epidermis of the palms or the soles becomes partially keratinized due to frequently repeated contact of the hands or feet with a variety of hard or coarse surfaces. Such calluses or corns crack due to, for example, dry or cold weather, thus allowing the dermis under the epidermis to be damaged. Therefore, it is necessary to periodically remove such calluses or corns from the hands or the feet. Such removal of calluses or corns from the hands or feet is commonly called "a pedicure".

It is typical and preferable to perform such a pedicure while bathing. That is, it is preferred to manually perform such pedicure for calluses or corns after sufficiently soaking the hands or the feet in hot water while bathing. In such a case, a pumice stone or a jutted pedicurer, having a coarse abrasive surface, has been typically used for manually filing the calluses or the corns of the sufficiently soaked palms or soles to remove the calluses or the corns.

However, the conventional pumice stone and jutted pedicurer force a user to repeatedly and strongly file the skin around the calluses or the corns with the pedicurer firmly gripped in one hand, and so it is very difficult for aged people or invalids to use the conventional pedicurers. Another problem experienced in the conventional pedicurers is that some of them have excessively coarse surfaces, unexpectedly damaging the dermis while performing a pedicure.

BRIEF SUMMARY OF THE INVENTION

Accordingly, the present invention has been made keeping in mind the above problems occurring in the prior art, and an object of the present invention is to provide a pedicure sander, which is provided with a motorized cylindrical rotary body fixedly covered with abrasive sheets and protected by a safety housing, having a plurality of different-sized openings formed on its bottom surface, thus allowing a user to smoothly, gradually and effectively remove a callus or a corn from the hands or the feet using an abrasive sheet exposed through a proper one of a large or small opening in accordance with a size of an area around the callus or the corn while rotating the rotary body at a desired low or high speed and visually checking the pedicuring effect, and being less likely to damage the dermis, and which also allows flakes of epidermis to be collected at one place while performing a pedicure, thus allowing the user to easily and cleanly carry out the pedicure.

In order to accomplish the above object, an embodiment of the present invention provides a pedicure sander, comprising: a cylindrical rotary body having two axial fixing grooves on its external surface; two abrasive sheets closely covering the external surface of the rotary body while being individually fixed to an associated one of the two fixing grooves at its opposite ends; a drive motor having a drive shaft fixedly set along the central axis of the rotary body; a handle seating the drive motor therein and being used as a manipulation grip of the sander; a support bracket rotatably holding the opposite ends of the drive shaft of the rotary body and having both a small-sized opening and a large-sized opening on its bottom surface; a safety housing rotatably mounted to one end of the support bracket and used for protecting the rotary body from the outside; a flake brush rotatably mounted to the support bracket using a hinge shaft, and provided with a bristle part for selectively coming into contact with the filing surface of the abrasive sheet at the bristle part to remove deposited flakes of epidermis from the filing surface; a torsion spring fitted over the hinge shaft of the flake brush and held against both the flake brush and the support bracket at its opposite arms, thus normally biasing the flake brush in one direction separating the bristle part from the filing surface of the abrasive sheet; and a shock absorbing unit provided at each end of the drive shaft, and consisting of a support bushing used for supporting the drive shaft, and a support spring normally biasing the support bushing upward within a casing.

BRIEF DESCRIPTION OF THE SEVERAL VIEWS OF THE DRAWINGS

The above and other objects, features and other advantages of the present invention will be more clearly understood from the following detailed description taken in conjunction with the accompanying drawings.

DETAILED DESCRIPTION OF THE INVENTION

Figure 1:
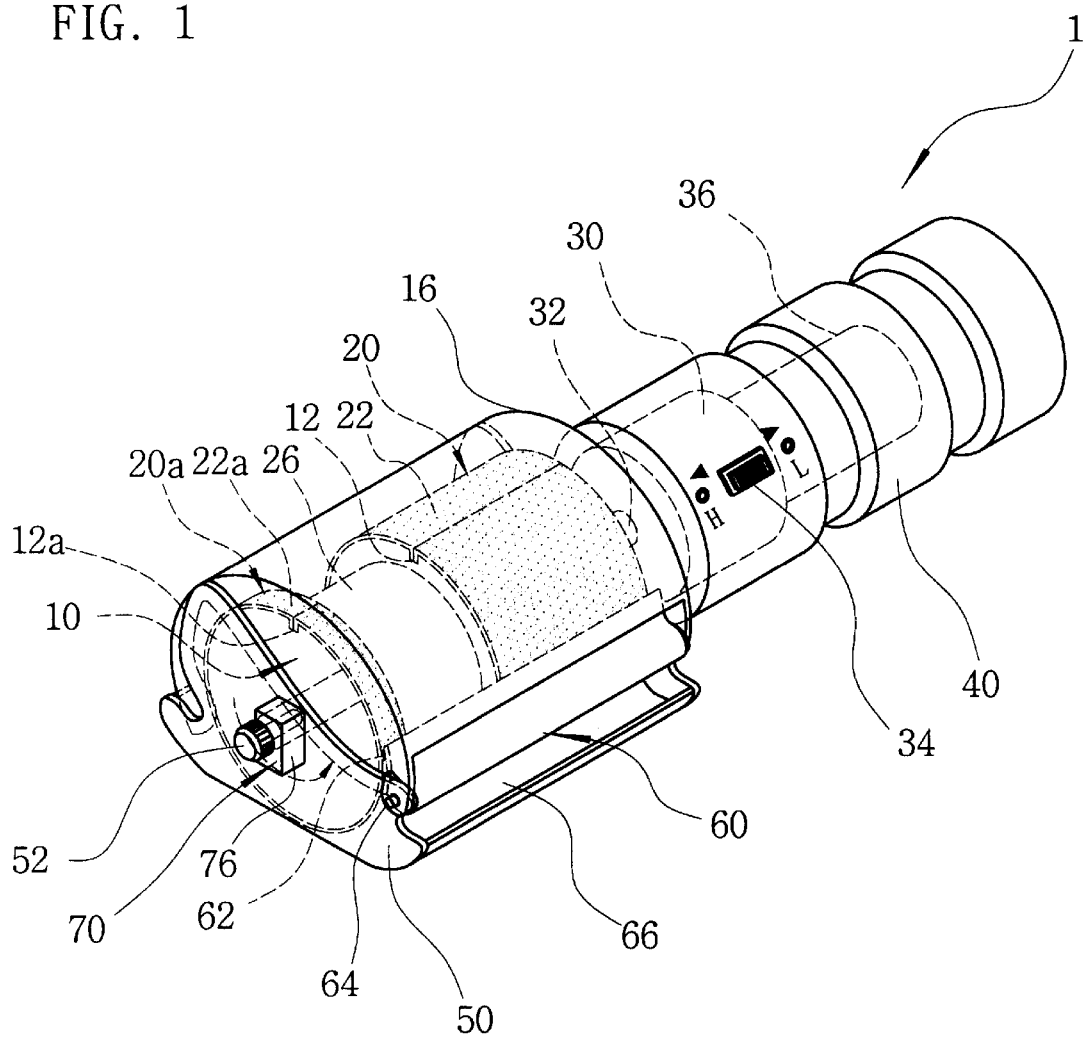
FIG. 1 is a perspective view, showing the construction of a pedicure sander in accordance with the preferred embodiment of the present invention.
Figure 2:
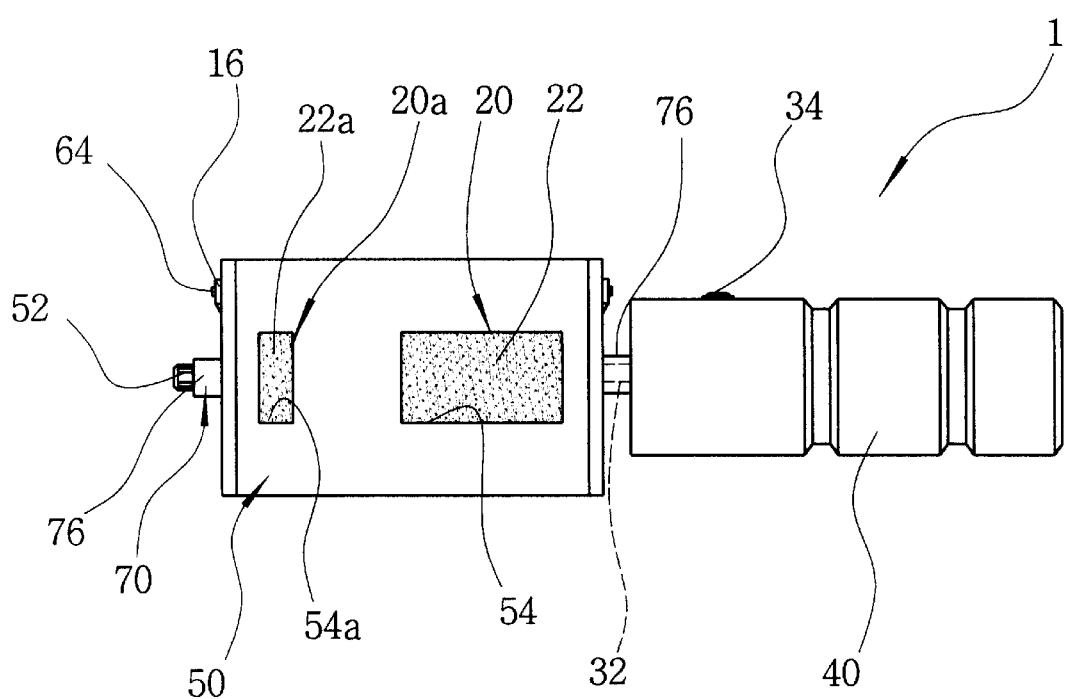
FIG. 2 is a bottom plan view of the pedicure sander of this invention.
Figure 3A:
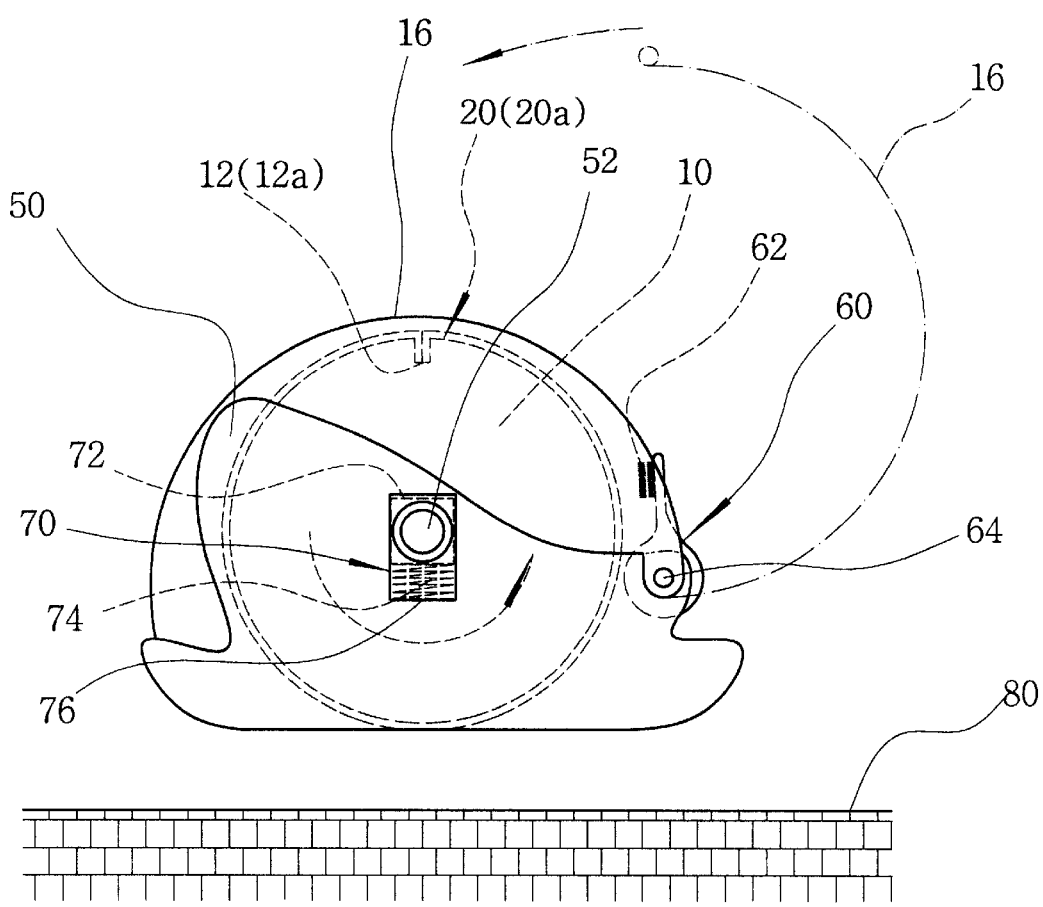
FIG. 3a is a side plan view of the pedicure sander of this invention at a stage just before the sander is brought into contact with the epidermis.
Figure 3B:
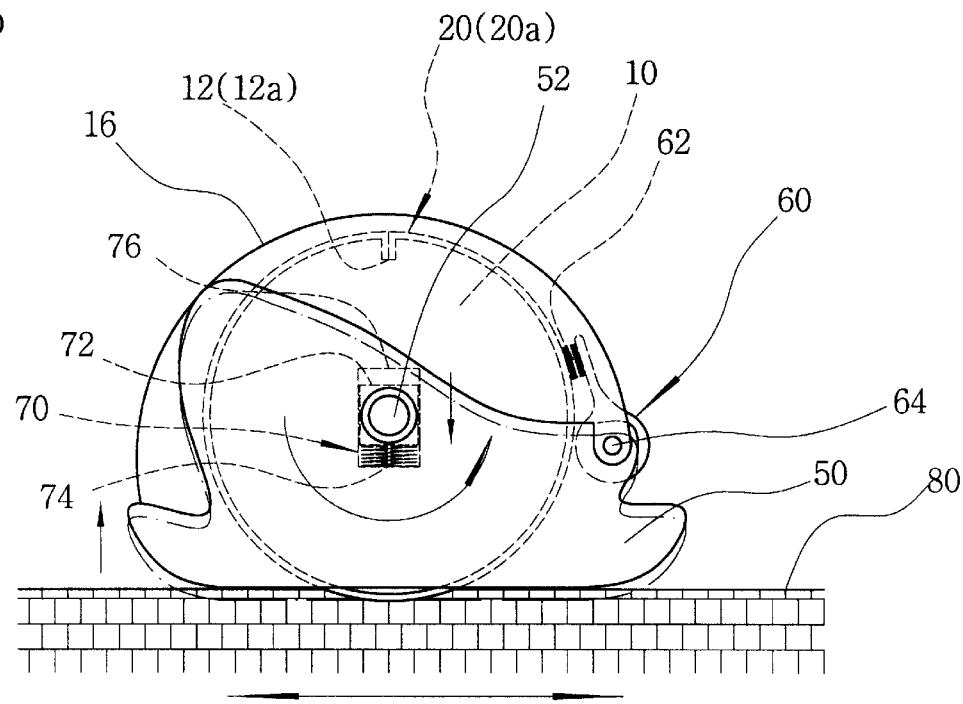
FIG. 3b is a side plan view of the pedicure sander of this invention while performing a pedicure.
Figure 3C:
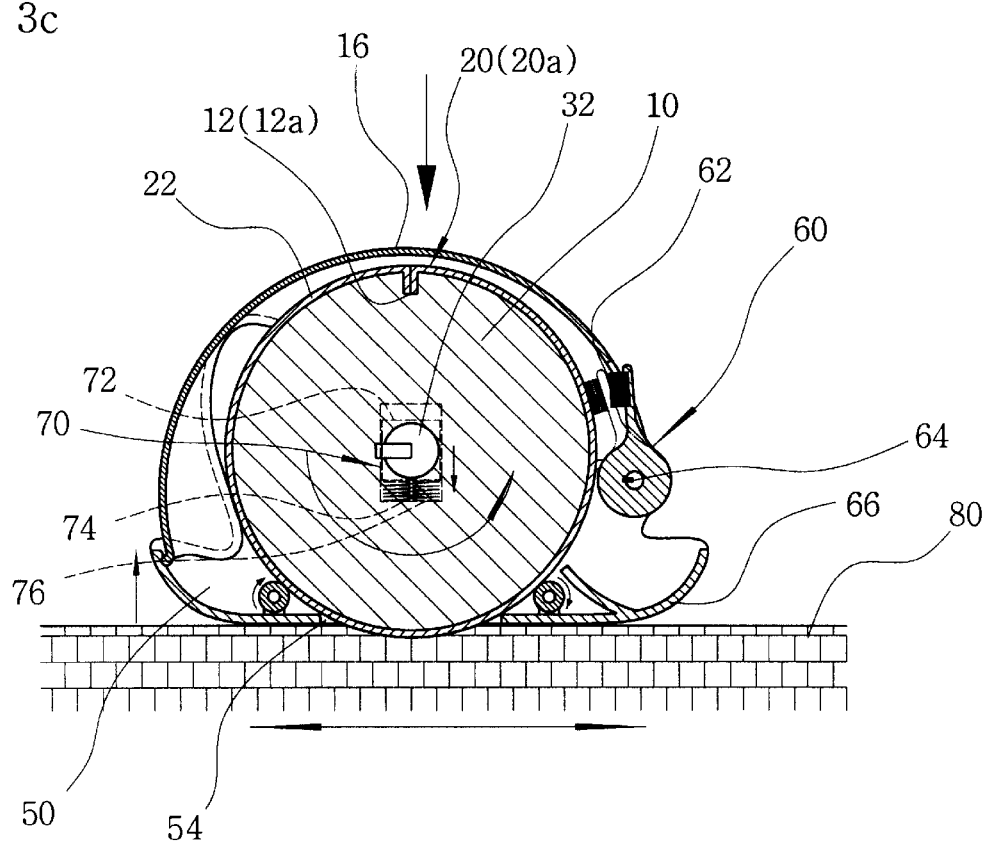
FIG. 3c is a side plan view of the pedicure sander of this invention, particularly showing a collection of flakes of epidermis while performing a pedicure.

FIG. 1 is a perspective view, showing the construction of a pedicure sander in accordance with the preferred embodiment of this invention. FIG. 2 is a bottom view of the above pedicure sander. FIG. 3a is a side view of the pedicure sander at a stage just before the sander is brought into contact with the epidermis. FIG. 3b is a side view of the pedicure sander while performing a pedicure. FIG. 3c is a side view of the pedicure sander, particularly showing a collection of flakes of epidermis while performing a pedicure.

As shown in the drawings, the pedicure sander 1 of this invention has a cylindrical rotary body 10, rotatably held by a bracket 50 at its drive shaft 32 and covered with a safety housing 16 at its top. In the present invention, the rotary body 10 may be preferably formed of a pumice stone or a float stone. However, it is more preferable to make the body 10 using a plastic material or metal. The drive shaft 32 is fixedly set along the central axis of the body 10. The rotary body 10 also has two axial fixing grooves 12 and 12a on its external surface such that the two grooves 12 and 12a are arranged in a line. Each of the two fixing grooves 12 and 12a firmly holds opposite ends of an associated one of two abrasive sheets 20 and 20a, thus allowing the two sheets 20 and 20a to closely and firmly cover desired parts of the external surface of the body 10 without being undesirably removed from the body 10.

The rotary body 10 is a cylindrical body, stepped on its external surface at a predetermined portion to form two large diameter annular parts at opposite end portions and a small diameter part 26 defined between the two large diameter annular parts. Of the two large diameter annular parts, one has a large width, while the other has a small width. The two fixing grooves 12 and 12a are formed on the two large diameter annular parts, with the two abrasive sheets 20 and 20a covering the two large diameter annular parts to form a wide abrasive part 22 and a narrow abrasive part 22a.

In such a case, the narrow abrasive part 22a with the narrow abrasive sheet 20a is preferably usable for filing the epidermis 80 around a callus or corn having a small area, while the wide abrasive part 22 covered with the wide abrasive sheet is preferably used for filing the epidermis 80 around a callus or corn having a large area.

The opposite ends of the drive shaft 32 of the rotary body 10 are held by a support bracket 50 so as to allow the body 10 to be smoothly rotatable relative to the bracket 50. In such a case, one end of the shaft 32 is rotatably held on the bracket 50 using a bearing means (not shown), such as a ball bearing, while the other end of the shaft 32 is rotatably held on the bracket 50 using both a bearing means (not shown) and a cap nut 52.

A shock absorbing unit 70 is provided at each end of the drive shaft 32. Each of the two shock absorbing units 70 comprises a support bushing 72 and a support spring 74, which are encased in a casing 76.

A flake brush 60 is mounted to a sidewall of the support bracket 50 at its rotatable shaft 64, with a torsion spring 68 fitted over the shaft 64 and held against both the brush 60 and the bracket 50 at its opposite arms. This torsion spring 68 normally biases the handle of the brush 60 together with the shaft 64 in one direction where the bristle part 62 of the brush 60 is separated from the abrasive sheets 20 and 20a of the rotary body 10 at a predetermined gap.

Two different-sized openings 54 and 54a are formed on the bottom surface of the support bracket 50 as best seen in FIG. 2 to allow the two abrasive parts 22 and 22a of the rotary body to be partially exposed outside the bottom surface of the bracket 50. Of the two openings 54 and 54a, the first one 54 has a large space corresponding to the size of the wide abrasive part 22, while the second one 54a has a small space corresponding to the size of the narrow abrasive part 22a.

A longitudinal flake collector 66 is fixed to the bracket 50 at a position under the flake brush 60, and collects flakes of epidermis or other detritus, which are removed from the abrasive sheets 20 and 20a by the bristle part 62 of the brush 60 during a pedicure.

The safety housing 16, covering the rotary body 10, is rotatably mounted to the front end of the flake brush shaft 64 at its front end. This safety housing 16 thus protects the rotary body 10 from external impact, and protects a user from being carelessly injured by the rotary body 10 during a pedicure. The rear end of the safety housing 16 is elastically held by the support bracket 50.

The drive motor 30 for the rotary body 10 is fixedly set within the handle 40 of the pedicure sander 1. The drive shaft 32 of the rotary body 10 integrally and axially extends from the drive motor 30. A rechargeable battery 36 for the motor 30 is set within the handle 40 at a position around the motor 30, while a control switch 34 is provided on the sidewall of the handle 40 for allowing a user to control rpm speed of the motor 30 as desired. Of course, the motor 30 may be driven by electric power supplied from a plug socket (not shown) through a cord (not shown).

In the present invention, it is preferable to provide two charge lamps (not shown), such as a charge warning lamp and a charge completion indicating lamp, on the sidewall of the handle 40 for informing a user of the state of the battery 36 to be charged and the state of completion of charge.

The assembling process and operational effect of the above pedicure sander 1 will be described herein below.

In order to assemble the parts of the sander 1 into a single body, the external surfaces of the wide and narrow annular parts of the rotary body 10 are fixedly covered with two abrasive sheets 20 and 20a. In such a case, the free end of each sheet 20 or 20a is primarily fixed in an associated fixing groove 12 or 12a of the body 10 prior to closely wrapping the sheet 20 or 20a around the wide and narrow annular part of the body 10. After the sheet 20 or 20a is completely and closely wrapped around the body 10, the sheet 20 or 20a is cut at a proper position to form another end, which is also fixed in the groove 12 or 12a. In such a case, it is necessary to carefully adjust the cut position of the sheet 20 or 20a to allow the sheet 20 or 20a to closely cover the rotary body 10. Therefore, the wide and narrow abrasive parts 22 and 22a are formed on the body 10. The rotary body 10 with the two abrasive parts 22 and 22a is, thereafter, set within the safety housing 16 while being held by the support bracket 50, and so the pedicure sander 1 of this invention is completely assembled.

In order to perform a pedicure using the sander 1, the sander 1 is turned on by connecting the plug of the cord (not shown) to a plug socket (not shown) or using power of the rechargeable battery 36. In such a case, rpm of the motor 30 can be controlled as desired by manipulating the control switch 34 of the handle 40. The controlled rotating force of the motor 30 is thus transmitted to the shaft 34 of the rotary body 10, and rotates the shaft 34 together with the body 30 at a desired speed.

The activated sander 1 is, thereafter, applied to a desired area of a foot or a hand having a target corn or a target callus, with the handle 40 gripped in one hand. When the target corn or callus is thick and/or has a large area, it is preferable to use the wide abrasive part 22 of the rotary body 10. In such a case, the sander 1 is applied to the target area such that the bottom surface of the sander 1 around the large-sized opening 54 is brought into contact with the epidermis 80. The sander 1 is, thereafter, properly pressed against the epidermis 80.

When the sander 1 is properly pressed against the skin as described above, the rotating shaft 32 of the body 10 is forced to move downward relative to the bracket 50. In such a case, the shaft 32 moves together with the support bushing 72 within the casing 76 of the shock absorbing unit 70 while compressing the support compression spring 74. Therefore, the body 10 moves from its fully retracted position inside the bracket 50 as shown in FIG. 3a to an extended position as shown in FIG. 3b.

Figure 4A:
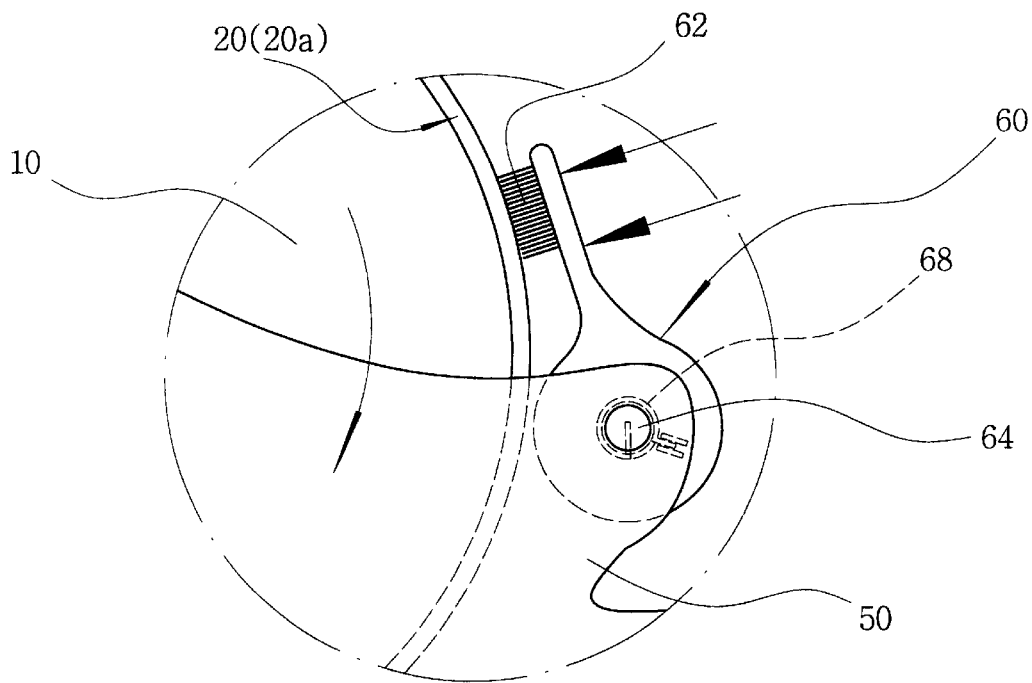
FIG. 4a is a side plan view, showing a spring-biased flake brush commonly held against the external surfaces of the abrasive sheets of the pedicure sander of this invention by an external biasing force to remove flakes of epidermis or other detritus from the abrasive sheets while performing a pedicure.
Figure 4B:
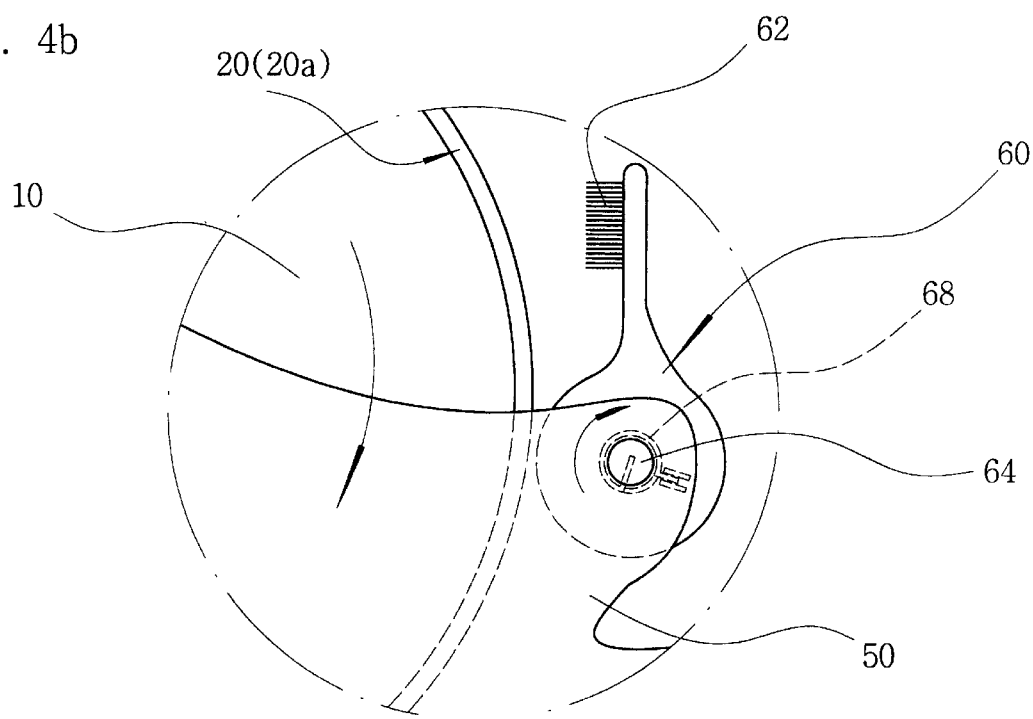
FIG. 4b is a side plan view, showing the flake brush returned to its original position, separated from the external surfaces of the abrasive sheets of the pedicure sander of this invention, due to the restoring force of a torsion spring after the brush is released from the external biasing force.

In the extended position of the rotary body 10 of FIG. 4b, the two abrasive sheets 20 and 20a of the body 10 are partially exposed outside the bottom surface of the support bracket 50 through the two openings 54 and 54a.

After the epidermis 80 around the target corn or callus is removed to a desired thickness by the abrasive sheet 20 of the wide abrasive part 22 exposed outside the bottom surface of the bracket 50 through the large-sized opening 54, the sander 1 is removed from the epidermis 80.

When the sander 1 is removed from the epidermis 80 as described above, the sander 1 is released from pressure applied from the epidermis 80, and so the rotary body 10 is elastically moved upward within the casing 76 to restore its retracted position of FIG. 4a due to the restoring force of the compression spring 74. Of course, it is necessary to design the restoring force of the spring 74 such that the spring 74 normally biases the body 10 to the retracted position when the sander 1 is free from any external pressure.

In such a case, the spring 74 pushes the bushing 72 together with the shaft 32 of the rotary body 10 upward, and so the abrasive parts 22 and 22a with the sheets 20 and 20a are fully retracted into the openings 54 and 54a of the support bracket 50.

When it is desired to remove a remaining part of the corn or callus from the previously filed epidermis 80, it is preferable to use the narrow abrasive part 22a of the rotary body 10. In such a case, the sander 1 is applied to the target area such that the bottom surface of the sander 1 around the small-sized opening 54a is brought into contact with the epidermis 80. The sander 1 is, thereafter, properly pressed against the epidermis 80.

When the sander 1 is properly pressed against the skin as described above, the rotary body 10 is forced to move downward relative to the bracket 50, thus changing in its position from the fully retracted position inside the bracket 50 to the extended position in the same manner as that described above. In the extended position of the rotary body 10, the two abrasive sheets 20 and 20a of the body 10 are partially exposed outside the bottom surface of the support bracket 50 through the two openings 54 and 54a. It is thus possible to remove the epidermis 80 around the remaining part of the corn or callus to a desired thickness using the narrow abrasive sheet 20a partially exposed outside the bottom surface of the bracket 50 through the small-sized opening 54a.

During such a pedicure, it is possible to easily control the filed thickness of the epidermis 80 as desired by controlling the rpm of the rotary body 10 using the finger-operable switch 34 of the handle 40.

FIG. 4a is a side view, showing the spring-biased flake brush 60 commonly held against the external surfaces of the abrasive sheets 20 and 20a of the pedicure sander 1 by external biasing force to remove flakes of epidermis or other detritus from the abrasive sheets 20 and 20a while performing a pedicure. FIG. 4b is a side view, showing the flake brush 60 returned to its original position, separated from the external surfaces of the abrasive sheets 20 and 20a, due to the restoring force of the torsion spring 68 after the brush is released from the external biasing force.

As shown in the drawings, flakes of epidermis 80 or other detritus are gradually deposited on the filing surfaces of the abrasive sheets 20 and 20a of the rotary body 10 during a pedicure, thus finally failing to perform a desired filing function when the filing surfaces become smooth due to deposited flakes of epidermis 80 or other detritus.

In such a case, it is necessary to remove the deposited flakes of epidermis 80 or other detritus from the filing surfaces of the sheets 20 and 20a. In order to accomplish such a removal of the flakes of epidermis 80 or other detritus from the sheets 20 and 20a, a user biases the flake brush 60 toward the rotary body 10 by hand while rotating the body 10 as shown in FIG. 4a. The brush 60 is thus rotated around the shaft 64 and is brought into frictional contact with the filing surfaces of the sheets 20 and 20a at its bristle part 62.

Therefore, the bristle part 62 of the brush 60 effectively removes to the flakes of epidermis 80 or other detritus from the filing surfaces of the sheets 20 and 20a.

The flakes of epidermis 80 or other detritus removed from the filing surfaces of the sheets 20 and 20a are received by the longitudinal flake collector 66 fixed to the bracket 50 at a position under the flake brush 60.

After the flakes of epidermis 80 or other detritus are sufficiently removed from the filing surfaces of the sheets 20 and 20a, the flake brush 60 is released from the applied pressure.

Therefore, the flake brush 60 is elastically rotated clockwise in the drawings due to the restoring force of the torsion spring 68, thus being automatically returned to its original position separated from the external surfaces of the abrasive sheets 20 and 20a as shown in FIG. 4b.

After removing the flakes of epidermis 80 or other detritus from the filing surfaces of the sheets 20 and 20a and separating the flake brush 60 from the external surfaces of the abrasive sheets 20 and 20a as described above, it is possible for the pedicure sander 1 to effectively perform a pedicure.

When the abrasive sheets 20 and 20a are repeatedly used for such pedicures for a lengthy period of time, the filing surfaces of the sheets 20 and 20a become smooth due to abrasion, and finally lose their desired filing function, thus requiring replacement with new sheets. In such a case, the cap nut 52 is loosened from the drive shaft 32 of the rotary body 10 prior to disassembling the safety housing 16, the support bracket 50 and the flake brush 60 from the sander 1. Thereafter, the opposite ends of each existing abrasive sheet 20 or 20a are removed from an associated fixing groove 12 or 12a of the rotary body 10 prior to replacing the two existing sheets 20 and 20a with new abrasive sheets. After the replacement of the abrasive sheets 20 and 20a, the safety housing 16, the support bracket 50 and the flake brush 60 are attached to the sander 1 prior to tightening the cap nut 52 to the drive shaft 32 of the rotary body 10.

Of course, when the pedicure sander 1 of this invention is used for public purpose within, for example, a beauty salon, it is necessary to limit the use of the abrasive sheets 20 and 20a such that they must be replaced with new sheets after they are used on a person.

As described above, the present invention provides a pedicure sander, provided with a motorized cylindrical rotary body fixedly covered with abrasive sheets and protected by a safety housing having a plurality of different-sized openings on its bottom surface. This sander thus allows a user to smoothly, gradually and effectively remove a callus or a corn from the hands or the feet using the abrasive sheets while controlling the rpm of the rotary body and visually checking the pedicure effect. The pedicure sander is less likely to damage the dermis, and allows the user to select a proper one of a large or small opening in accordance with a size of an area around the callus or the corn during a pedicure. Another advantage of this pedicure sander is that it allows flakes of epidermis to be collected at one place, thus allowing the user to easily and cleanly carry out the pedicure.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A pedicure sander, comprising:

a cylindrical rotary body having an axial fixing groove on its external surface;

an abrasive sheet closely covering an external surface of said rotary body while being fixed to said fixing groove at its opposite ends;

a drive motor comprised of a drive shaft, said drive shaft being fixedly set along a central axis of said rotary body;

a handle seating said drive motor therein and being used as a manipulation grip of the sander;

a support bracket rotatably holding the opposite ends of the drive shaft of said rotary body and having both a small-sized opening and a large-sized opening on its bottom surface;

a safety housing rotatably mounted to one end of said support bracket and used for protecting said rotary body from the outside;

a flake brush rotatably mounted to said support bracket using a hinge shaft, said brush being comprised of a bristle part for selectively coming into contact with a filing surface of said abrasive sheet at the bristle part to remove deposited flakes of epidermis from said filing surface;

a torsion spring fitted over said hinge shaft of the flake brush and held against both the flake brush and the support bracket at its opposite arms, thus normally biasing the flake brush in one direction separating the bristle part from the filing surface of the abrasive sheet; and a shock absorbing unit provided at each end of said drive shaft, said shock absorbing unit comprising a support bushing used for supporting the drive shaft, and a support spring normally biasing said support bushing upward within a casing.

* * * * *